(12) United States Patent
Thrailkill et al.

(10) Patent No.: US 7,775,679 B2
(45) Date of Patent: Aug. 17, 2010

(54) HIGH INTENSITY LIGHT SOURCE FOR A MACHINE VISION SYSTEM AND METHOD OF MAKING SAME

(75) Inventors: William Thrailkill, Rochester, VT (US); John E. Thrailkill, Shelburne, VT (US)

(73) Assignee: Advanced Illumination, Inc., Rochester, VT (US)

( * ) Notice: Subject to any disclaimer, the term of this patent is extended or adjusted under 35 U.S.C. 154(b) by 403 days.

(21) Appl. No.: 11/194,905

(22) Filed: Aug. 1, 2005

(65) Prior Publication Data

US 2006/0039141 A1 Feb. 23, 2006

Related U.S. Application Data

(60) Provisional application No. 60/602,563, filed on Aug. 18, 2004.

(51) Int. Cl.
F21V 1/00 (2006.01)
F21V 3/00 (2006.01)

(52) U.S. Cl. .................. 362/237; 362/238; 362/239; 362/240; 362/244; 362/249.02; 362/255; 362/256; 362/277; 362/282; 362/319; 362/322; 362/311.02; 362/311.14; 362/331; 362/800

(58) Field of Classification Search .................. 362/341, 362/237–240, 282–283, 242, 244, 246, 249.02, 362/255–256, 267–268, 277, 319, 322, 294, 362/311.02, 311.14, 331–332, 800; 356/237.1; 250/559.4; 348/125
See application file for complete search history.

(56) References Cited

U.S. PATENT DOCUMENTS

| | | | | | |
|---|---|---|---|---|---|
| 5,615,052 | A | * | 3/1997 | Doggett | 359/811 |
| 5,822,053 | A | * | 10/1998 | Thrailkill | 356/237.1 |
| 6,132,072 | A | * | 10/2000 | Turnbull et al. | 362/494 |
| 6,428,189 | B1 | * | 8/2002 | Hochstein | 362/373 |
| 6,547,423 | B2 | * | 4/2003 | Marshall et al. | 362/333 |
| 6,614,103 | B1 | * | 9/2003 | Durocher et al. | 257/678 |
| 6,961,190 | B1 | * | 11/2005 | Tamaoki et al. | 359/726 |
| 6,986,593 | B2 | * | 1/2006 | Rhoads et al. | 362/308 |
| 7,175,299 | B2 | * | 2/2007 | Uke et al. | 362/187 |
| 7,181,378 | B2 | * | 2/2007 | Benitez et al. | 703/2 |
| 2007/0285920 | A1 | * | 12/2007 | Seabrook | 362/240 |

* cited by examiner

*Primary Examiner*—Sandra L O'Shea
*Assistant Examiner*—Sean P Gramling
(74) *Attorney, Agent, or Firm*—Cesari and McKenna, LLP

(57) ABSTRACT

A light source for machine vision applications includes a housing having a thermally conductive base plate which supports an array of high intensity LEDs. The LEDs are fitted with secondary lenses which are aimed such that the light beams from the LEDs illuminate fixed targets having a predetermined spatial relationship so that the light source produces a very uniform light field. After the lenses are aimed, they are secured in the desired position relative to their associated LEDs using a UV-curable adhesive.

14 Claims, 4 Drawing Sheets

HIGH INTENSITY LIGHT SOURCE FOR A MACHINE VISION SYSTEM AND METHOD OF MAKING SAME

CROSS-REFERENCE TO RELATED APPLICATIONS

The present application claims the benefit of U.S. Provisional Patent Application Ser. No. 60/602,563, which was filed on Aug. 18, 2004, by William Thrailkill et al. for a HIGH INTENSITY LIGHT SOURCE FOR A MACHINE VISION SYSTEM AND METHOD OF MAKING SAME and is hereby incorporated by reference.

FIELD OF THE INVENTION

This invention relates to a light source especially adapted for use with a machine vision system. It relates more particularly to a high-intensity backlight or light source for such a system.

BACKGROUND OF THE INVENTION

Machine vision relates to automated product inspection and is generally is used for quality inspection during product manufacturing. The basic elements used in a machine vision system are similar to those employed by a human inspector, namely: 1) a sensor (i.e., the eye) to take a picture of the object under inspection; and 2) a comparator (i.e., the brain) which compares the picture formed by the sensor against a known reference. Thus, in its simplest form, a machine vision system compares a picture of what it sees against a known reference.

A typical system of this type includes a machine vision controller which controls the operation of a video camera and receives analog video data from the camera. The controller also provides control signals to control electronics which drive a light source or backlight. As the object to be inspected moves on a conveyer belt, for example, the object is illuminated with light from the light source, and the camera captures an image of the illuminated object. The camera then transmits a signal indicative of the image to the controller which compares the image against the known reference. If a captured image is outside a certain predetermined tolerance in comparison to the known reference, the object under inspection fails the inspection.

In recent years, light emitting diodes (LEDs) have become the dominant light sources in machine vision systems due primarily to the relatively small size, long life and fast switching speed which allows them to be used in a strobed mode or application. In the past, there has been no control over the direction of the beam of light emitted from each LED in the array. This is because, due to manufacturing tolerances, most LEDs are not ideal ones. As shown in FIG. 1A, the LED may be slightly out of alignment so that the light beam B emitted by the LED is not symmetrical about its optical axis O, i.e., it deviates therefrom as shown by angle $\alpha_1$, in that figure. To overcome that problem, a technique was devised for aiming, while mounting, even non-ideal LEDs in an array to compensate for such deviations such that the array provides a relatively uniform output; see U.S. Pat. No. 5,822,053, the contents of which are hereby incorporated herein by reference.

In accordance with that patent, the light source includes a housing with a rigid base plate. Each LED L (FIG. 1A) of the array is situated in a hole in the base plate and pointed such that the light emitted by the LED illuminates a known location. Each LED is then secured by a UV-curable cement such that it remains in its predetermined position.

While the mounting technique disclosed in that patent is suitable for mounting and aiming the relatively low-intensity (e.g. 20-60 milliwatts) LED L having electrical leads that suffice to conduct away heat from the LED, it cannot be used with the high intensity (e.g., 1-5 watts) LED HIL shown in FIG. 1B preferred for use in today's machine vision systems because of its superior radiation characteristics and longer operating life. The latter LED HIL has a current draw of 350-750 milliamps and thus generates much more heat than the conventional LED L. As such, the high intensity LED HIL requires a large-area heat sink slug which must be in intimate thermal contact with the light source base plate and/or housing in order to conduct away that heat. This means that such high-intensity LEDs cannot be anchored in holes in the housing base plate and be pointed in a predetermined manner as described in the above patent.

SUMMARY OF THE INVENTION

Accordingly, it is an object of the present invention to provide an improved high intensity light source for a machine vision system.

Another object of the invention is to provide such a light source which incorporates an array of high-intensity LEDs which combine to produce a uniform light field.

Yet another object is to provide such a light source for lighting small objects with more intensity or larger objects from greater distances.

A further object of the invention is to provide a practical method for making a light source comprising an array of high-intensity LEDs so that the source provides a uniform light field.

An additional object is to provide a method for aiming high current draw LEDs in an efficient and effective manner so that they can be used more widely in machine vision applications.

Other objects will, in part, be obvious and will, in part, appear hereinafter. The invention accordingly comprises the steps and the relation of steps with respect to each of the others and the features of construction, combination of elements and arrangements of parts which will be exemplified in the following detailed description, and the scope of the invention will be indicated in the claims.

Briefly, our light source comprises a housing having a thermally conductive base plate which supports an array of high-intensity LEDs. The housing may also include side walls which support a diffuser spaced a fixed distance from the LED array. The high intensity LEDs all have heat sinks which are in intimate thermal contact with the base plate and, during the mounting process to be described later, the LEDs are fitted with secondary lenses which are aimed such that the light beams from the LEDs illuminate corresponding fixed targets which have a predetermined spatial relationship so that the light source produces a very uniform light field.

As we shall see, after the secondary lenses are aimed or targeted, their positions are permanently fixed using a UV-curable cement or other suitable means or method.

Thus, by fitting the high-intensity LEDs with secondary lenses which can be aimed precisely to compensate for tolerance variations in the LEDs, there results a light source that produces a very uniform light-field. Moreover, fewer LEDs are required to illuminate an object under inspection as compared with prior comparable light sources used for machine vision inspection.

BRIEF DESCRIPTION OF THE DRAWINGS

For a fuller understanding of the nature and objects of the invention, reference should be made to the following detailed description taken in connection with the accompanying drawings, in which.

DETAILED DESCRIPTION OF AN ILLUSTRATIVE EMBODIMENT

Figure 1A:
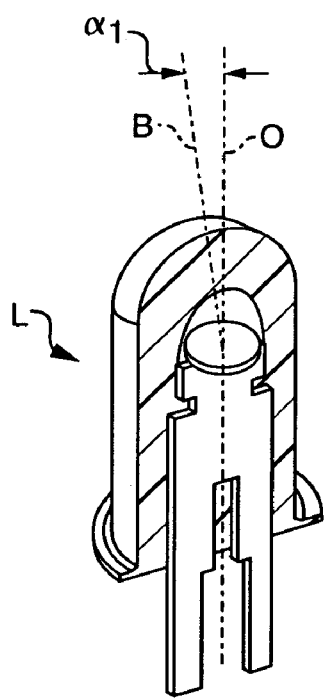
FIG. 1A, already described, is a sectional view of a conventional relatively low current draw, low intensity LED.
Figure 1B:
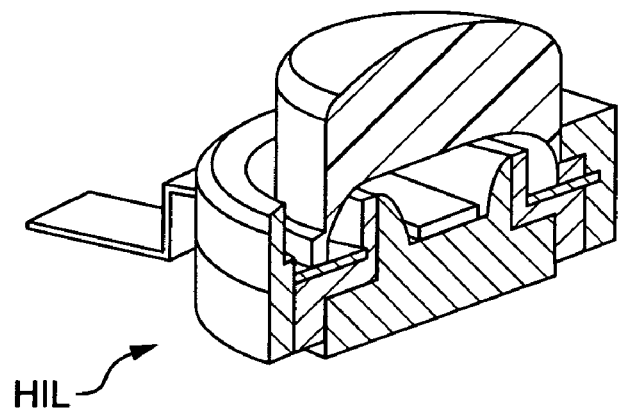
FIG. 1B, already described, is a similar view of a conventional high-current draw, high-intensity LED.
Figure 2:
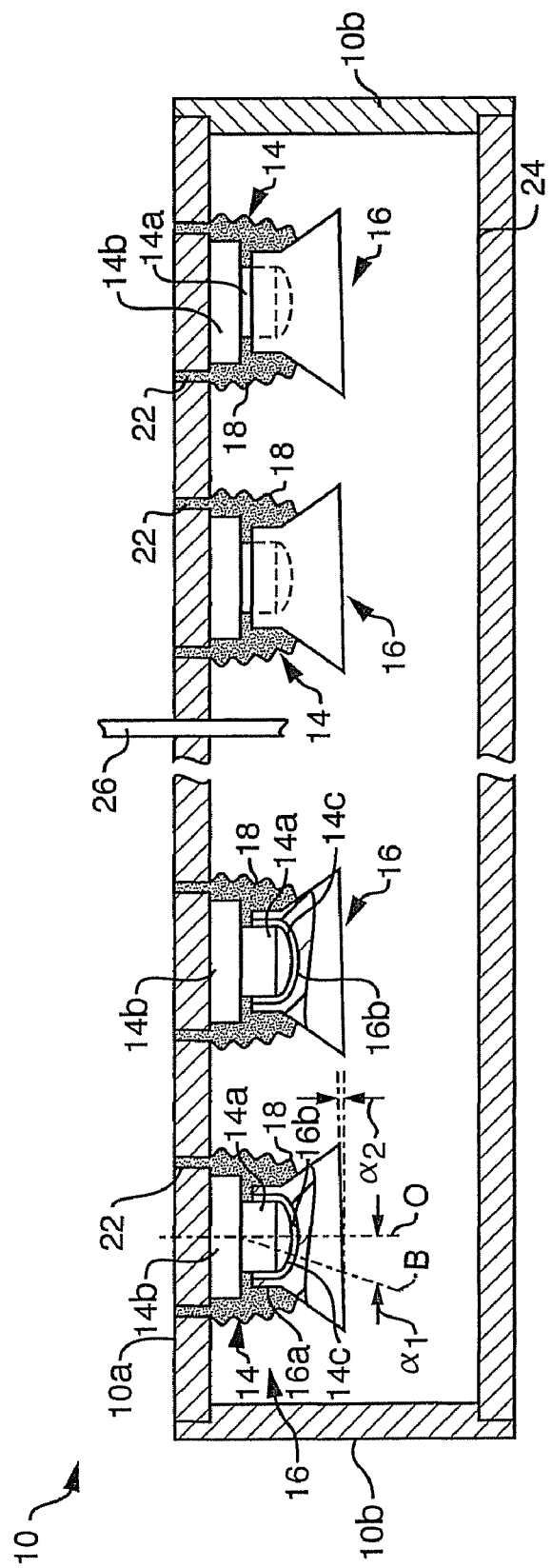
FIG. 2 is a sectional view on a much larger scale showing a light source comprising high-intensity lenses fitted with secondary lenses in accordance with the invention.

Refer now to FIG. 2, which illustrates a machine vision light source incorporating the invention. The light source includes a housing shown generally at 10 comprising a rigid base plate 10a which is highly thermally conductive. For example, it may be of copper metal. Mounted at spaced-apart locations on base plate 10a is a plurality of similar high-intensity LEDs 14. Each LED 14 may be similar to the LED HIL in FIG. 1B in that its main body 14a extends up from a heat sink slug 14b and it is topped off by a plastic lens 14c. LEDs such as this are available under the designation LUXEON. As shown in FIG. 2, each LED 14 is mounted to base plate 10a such that its heat sink slug 14b is in intimate thermal contact with and soldered to base plate 10a.

A given LED 14 may not be an ideal LED in that, due to manufacturing tolerances, a light beam B from the LED may not be symmetrical about the optical axis O of the LED; in other words, it may deviate by an angle $\alpha_1$, as shown at the left-hand LED 14 in FIG. 2.

To compensate for the aforesaid imperfections in LEDs 14, each LED is fitted with a secondary lens 16. Each lens 16 includes a collar 16a which may be engaged around or clipped onto the body 14a of the corresponding LED 14. Lens 16 has an interior surface 16b spaced somewhat from LED lens 14c and whose curvature corresponds to that of lens 14c so that the light beam emanating from LED 14 suffers minimum distortion upon passing through the secondary lens 16. Suitable lenses 16 are available from the Fraen Company.

Figure 3:
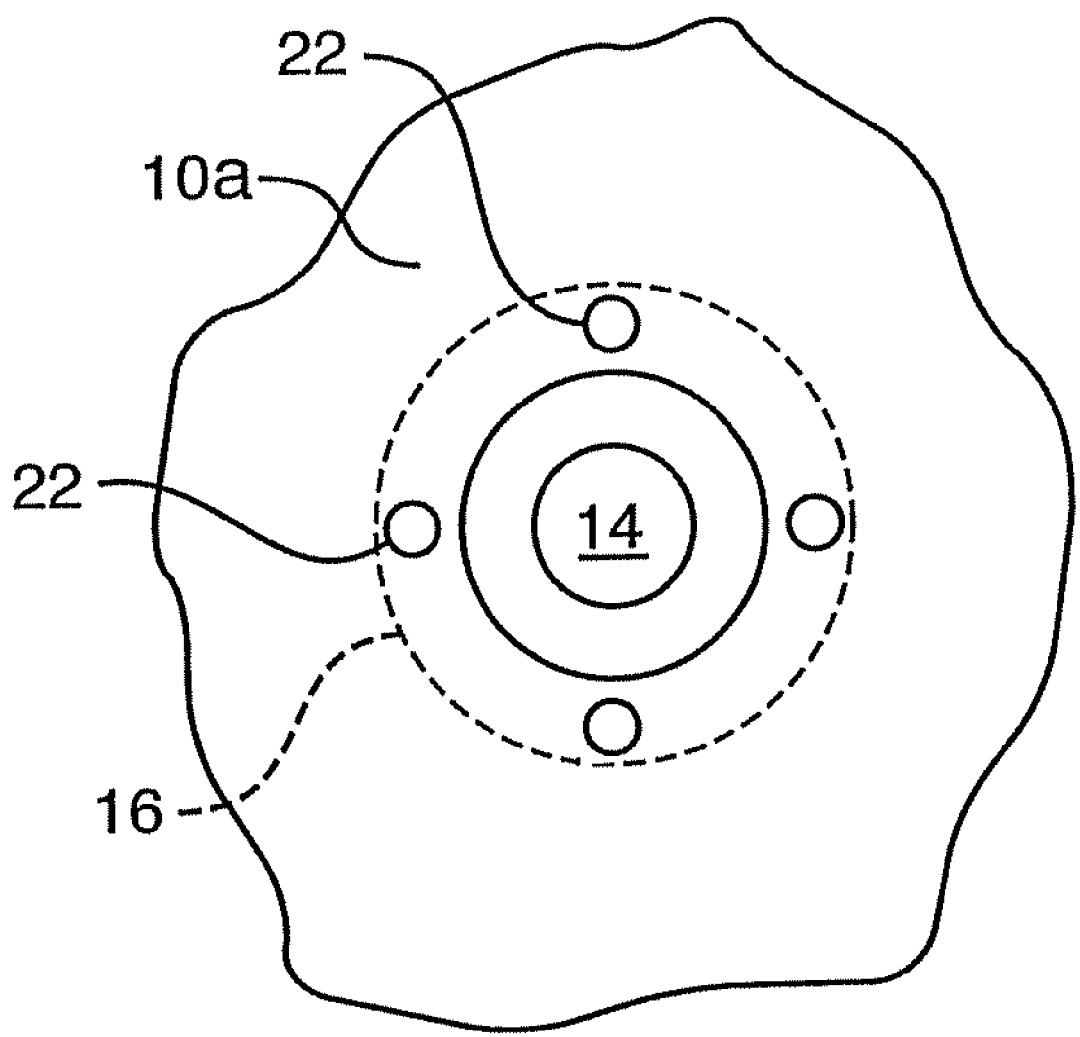
FIG. 3 is a fragmentary top plan view showing the right hand LED in FIG. 2 without its secondary lens.

As will be described in detail later, each lens 16 is movable, i.e., can tilt in all directions, to some degree on the corresponding LED 14 so that the lens 16 can be aimed in such a manner as to compensate for the asymmetry in the associated LED 14. For example, it may be tilted through an angle $\alpha_2$ as shown by the left hand lens 16 in FIG. 2. After it has been properly aimed or targeted, each lens 16 may be temporarily tacked in place by a small amount of UV-curable cement 18 or the like deposited between the lens 16 and the associated LED 14. Then, after all of the lenses 16 have been targeted as aforesaid, to maximize the strength of the securement of each lens 16 to the base plate 10a, cement 18 may be spread between each lens 16 and base plate 10a, all around each LED 14 and the entire array subjected to UV light until the cement 18 has fully cured. Most preferably, a plurality of recesses or through holes 22 are provided in base plate 12 around the periphery of each LED 14. As best seen in FIG. 3, in the illustrated light source, there are four holes or recesses 22 spaced 90° apart around the LEDs 14. In its fluid form, the cement 18 flows into the holes or recesses 22 so that after the cement is cured, each lens 16 is essentially "riveted" or permanently secured to base plate 10a.

Referring again to FIG. 2, housing 10 usually also includes side walls 10b which may support a diffuser 24 spaced a fixed distance from the LEDs 14 to optimize the light field uniformity from the source, and a power cord 26 which carries the electrical power and control signals to the array of LEDs 14.

Figure 5:
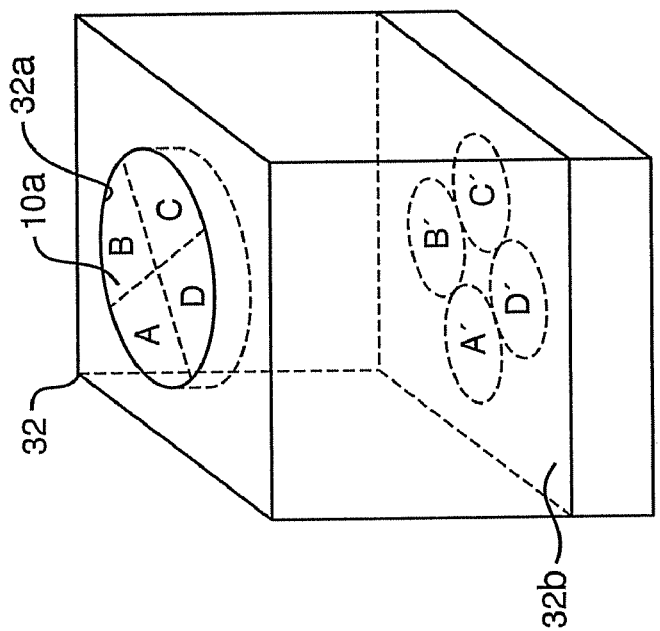
FIG. 5 illustrates an alignment fixture used to hold the base plate so that the secondary lenses on the LEDs can be aimed and fixated in a predetermined manner.
Figure 4:
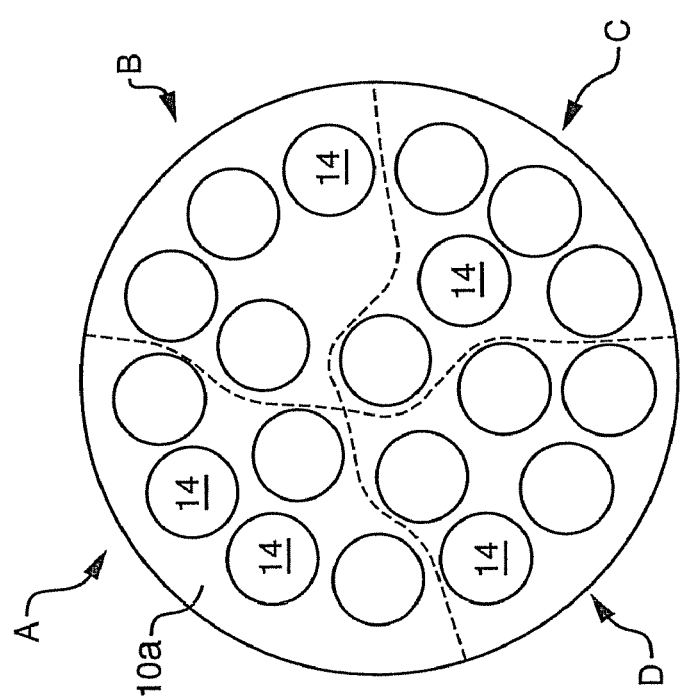
FIG. 4 is a bottom plan view showing a typical array of LEDs mounted to the base plate of the light source shown in FIG. 2.

FIG. 4 is a bottom plan view of base plate 10a supporting an array of twenty LEDs 14. In order to aim the secondary lenses 16 on those LEDs, the base plate 10a is seated in an aperture 32a of an alignment fixture 32 as shown in FIG. 5 such that the secondary lenses 16 on those LEDs are pointed at a bottom surface 32b of the alignment fixture. Ideally, that surface is separated from the LEDs by a distance which is equal to the distance the light source will be separated from the object intended to be illuminated in the machine vision system.

While mounted in the alignment fixture 32, power is applied in turn to each LED 14 such that the light emitted by the LED and projected through its lens 16 illuminates a predetermined location on the bottom surface 32b. As described in the above patent, the LEDs 14 mounted to base plate 10a can be divided into quadrants or sectors A-D, and the light emitted from the lens 16 associated with each LED will be pointed to illuminate a corresponding quadrant or sector A'-D' located on bottom surface 32b. Once the secondary lens 16 of a LED 14 is aimed so that it illuminates the area covered by its associated quadrant or sector, the UV curable adhesive 18 is applied and set to hold the lens in position. The specific procedure for aiming each secondary lens 16 is more or less the same as that described in the aforesaid patent for the low-intensity LEDs which were of concern in that patent, except that the adjustment is accomplished by moving and aiming the lenses 16 as opposed to the LEDs-themselves.

It can thus be seen that the objects set forth above, among those made apparent from the preceding description, are efficiently attained. Also, since certain changes may be made in carrying out the method and in the construction set forth herein without departing from the scope of the invention, it is intended that all matter contained in the above description or shown in the accompanying drawings shall be interpreted as illustrative and not in a limiting sense.

What is claimed is:

1. A light source for use in a machine vision system for substantially uniformly illuminating a predetermined area, comprising:

a base plate;

a plurality of high intensity light emitting diodes mounted at spaced apart positions to said base plate, each of said diodes including a main body topped off by a primary lens having a convex end surface facing away from the base plate and an optical axis extending through said lens, each diode when energized emitting a light beam, consisting of a collection of light rays, along a light beam axis which deviates angularly from said optical axis of the primary lens;

a secondary lens positioned over the primary lens of each of said diodes, each secondary lens including an interior surface spaced from, and having a concave curvature substantially coinciding with that of, the convex end surface of the primary lens over which it is positioned, and means for fixing the angular position of each secondary lens relative to the associated diode to compensate for said deviation so that the light beam transmitted by each secondary lens when its associated diode is energized is symmetric about the optical axis of said primary lens.

2. The light source of claim 1 in which said base plate is thermally conductive.

3. The light source of claim 2 in which each of said diodes includes a heat sink in thermal contact with said base plate.

4. The light source of claim 1 further including a curable adhesive between each of said secondary lenses and its associated diode which is cured to secure the secondary lens in place after it is adjusted.

5. The light source of claim 4 in which said base plate includes a plurality of recesses around each of said diodes mounted thereto and into which the curable adhesive extends.

6. The light source of claim 4 or 5 in which said adhesive is a liquid light-curable adhesive which is cured by exposing the adhesive to light.

7. The light source of claim 1 further including a diffuser spaced a fixed distance from the primary lenses of said diodes to optimize the light field uniformity from said light source.

8. The light source of claim 7 further including a housing for holding said base plate and said diffuser.

9. The light source of claim 1 in which each of said diodes has an intensity in the range of about 1 to about 5 watts.

10. A method of constructing a light source for use in a machine vision lighting system, said light source having a plurality of high intensity light emitting diodes mounted on a base plate for substantially uniformly illuminating a predetermined area, each including a main body topped off by a primary lens having a convex lens surface facing away from the base plate and an optical axis extending through said primary lens, said primary lens constituting the light-emitting end of the diode, each diode when energized emitting a light beam, consisting of a collection of light rays, along a light beam axis which deviates angularly from said optical axis of the primary lens, said method comprising the steps of:

mounting the diodes at spaced apart positions on the base plate so that the light-emitting end of each diode extends away from the base plate;

providing a secondary lens over the light-emitting end of each of the diodes, each secondary lens being moveable relative to the light-emitting end of the associated diode in three dimensions within a predetermined range of movement;

providing an alignment fixture for receiving the base plate and having a target surface spaced from the base plate and in optical communication with the light emitting end of each diode;

defining on the target surface a plurality of illumination sectors;

selectively illuminating one of the diodes and, while illuminated, angularly adjusting the secondary lens relative to the light-emitting end of the illuminated diode to compensate for said deviation until that light from the illuminated diode is focused substantially in one of the plurality of illumination sectors according to a predetermined lighting pattern;

repeating the selectively illuminating and adjusting steps for the other diodes on the base plate; and securing each secondary lens relative to its associated diode after it is adjusted.

11. The method of claim 10 further including the step of temporarily securing each secondary lens relative to its associated diode after it is adjusted.

12. The method of claim 11 in which the securing step comprises permanently securing all of the secondary lenses relative to their associated diodes after they are adjusted all at the same time.

13. The method of claim 11 or 12 in which the securing step comprises applying an uncured adhesive between the secondary lenses and their associated diodes and then curing the adhesive.

14. The method of claim 13 in which the uncured adhesive is a liquid light-curable adhesive and the curing step comprises exposing the adhesive to light.

\* \* \* \* \*